United States Patent [19]
Moore, Jr.

[11] Patent Number: 5,882,486
[45] Date of Patent: Mar. 16, 1999

[54] GLYCOL REFINING

[76] Inventor: John W. Moore, Jr., P.O. Box 1406, Guymon, Okla. 73942

[21] Appl. No.: 886,793

[22] Filed: Jul. 1, 1997

Related U.S. Application Data

[60] Provisional application No. 60/028,694 Oct. 18, 1996.

[51] Int. Cl.[6] .............................. B01D 3/06; B01D 3/10; C07C 27/28
[52] U.S. Cl. .............................. 203/87; 95/208; 95/209; 202/83; 202/186; 202/200; 202/205; 203/88; 203/91; 210/295; 210/774; 568/868
[58] Field of Search .................... 203/88, 87, 50, 203/18, 91; 202/205, 83, 186, 200; 95/209, 208; 568/868, 913; 159/2.1, 47.3, DIG. 16; 210/295, 774, 773, 799

[56] References Cited

U.S. PATENT DOCUMENTS

| | | | |
|---|---|---|---|
| 3,648,434 | 3/1972 | Gravis, III et al. | 95/209 |
| 3,841,382 | 10/1974 | Gravis, III et al. | 203/18 |
| 4,175,034 | 11/1979 | Thompson | 203/87 |
| 4,182,659 | 1/1980 | Anwer et al. | 568/868 |
| 4,233,267 | 11/1980 | Coker et al. | 202/205 |
| 4,375,977 | 3/1983 | Honerkamp et al. | 96/295 |
| 4,460,383 | 7/1984 | Valerius | 55/32 |
| 4,661,130 | 4/1987 | Ebeling et al. | 96/295 |
| 5,102,503 | 4/1992 | Silinski et al. | 202/83 |
| 5,116,393 | 5/1992 | Ebeling | 96/265 |
| 5,163,981 | 11/1992 | Choi | 95/209 |
| 5,262,013 | 11/1993 | Beal et al. | 203/18 |
| 5,624,534 | 4/1997 | Boucher et al. | 202/205 |

FOREIGN PATENT DOCUMENTS

| | | | |
|---|---|---|---|
| 3931013 | 3/1991 | Germany | 202/200 |

*Primary Examiner*—Virginia Manoharan
*Attorney, Agent, or Firm*—Wendell Coffee; Mark E. Scott

[57] ABSTRACT

Contaminated glycol is refined by vacuum distillation. Specifically the evaporator is heated to a temperature below the degradation temperature of the glycol. The vacuum is used to bring the flashpoint down sufficiently so that glycol evaporates or flashes at that temperature. The glycol is condensed and filtered through activated granular carbon. The principal use of refining the glycol is to refine the triethylene glycol used in natural gas dehydration plants. For such purposes the equipment is mounted upon a trailer to be taken to the plant for cleaning glycol. In such instance, in addition to refining the glycol, a cleaning agent (which contains a degreaser) is added to the refined glycol. The glycol is refined while the natural gas dehydration plant is in normal operation and therefore it is not necessary to stop the natural gas dehydration plant for refining the glycol used therein. In addition, by the addition of the cleaning agent, the dehydrating plant equipment may be cleaned while the plant is in normal operation. Another use for refining glycol is anti-freeze glycol. In such instances, the distillation temperatures will be much less but if the process is performed using the same equipment as natural gas, the absolute vacuum pressure will be about the same as before.

6 Claims, 2 Drawing Sheets

GLYCOL REFINING

CROSS REFERENCE TO RELATED APPLICATION

PROVISIONAL PATENT APPLICATION

Applicant filed a Provisional Application on this subject matter on Oct. 18, 1996, Ser. No. #60/028,694, now abandoned, John W. Moore, Jr., invention for Triethylene Glycol Refining. Specific reference is made to that document.

BACKGROUND OF THE INVENTION (1) Field of the Invention

This invention relates to recycling of fluids which have been polluted or contaminated. The majority of the fluids treated according to this invention are used in natural gas treating plants, primarily Triethylene Glycol (also called TEG). In addition, ethylene glycol and diethylene glycol, which find use as anti-freeze, also accumulate hazardous material and are recycled by this process.

Operators of natural gas dehydration and treatment plants will have ordinary skill in this art.

(2) Description of the Related Art

Natural gas flowing from wells may contain water vapor, liquid water, brine solution, heavy and light hydrocarbons, and particulate matter such as sand, pipeline scale and rust. If these elements remain in the gas stream they will cause numerous problems in the pipeline and processing equipment. Treating natural gas will commonly occur at individual wells, gathering systems, compressor stations, distribution stations, and gas processing units. Lowering the water content of natural gas at these sites will prevent the clogging of pipelines due to hydrate formation. Hydrate formation will occur with the combining of water and natural gas molecules. Hydrates will block valves and flowmeters. Hydrates will also accumulate at low points in the pipeline. Hydrates will decrease pipeline efficiency and cause shutdowns. The hydrates will also increase erosion and corrosion. To prevent the formation of hydrates, natural gas must be dehydrated at the aforementioned sites prior to reaching the pipeline.

Processes for removal of entrained water vapor and other contaminants in natural gas are well known. The most common process for the removal of water in natural gas is glycol dehydration. The process is done in a natural gas dehydration plant. Where TEG is the preeminent desiccant used in the dehydration process. TEG offers the following advantages: 1) ability to absorb large amounts of water, 2) relatively low solubility of valuable gas constituents, 3) chemical stability, 4) easy to regenerate, and 5) low cost. Before treating natural gas with glycol dehydration, the wet natural gas passes through an inlet separator where water droplets, liquid hydrocarbons, entrained sand, rust and so forth are separated out of the gas stream. The wet natural gas then flows to the absorber or contacting tower where it is interfaced with the TEG. The wet natural gas will enter the contacting tower at the bottom where it will flow upward, while lean TEG, free of water, will enter the top of contacting tower where the TEG flows downward. The counter current flow will aid the lean TEG in absorbing most of the water contained in the natural gas. The natural gas stream leaving the tower is said to be dehydrated. The TEG leaving the tower is called rich TEG. The rich TEG is passed through sock filters to remove any particulate matter picked up by the TEG. The rich TEG then flows to a reboiler or regenerator where it is heated to drive off any of the absorbed water contained in the rich TEG solution. After the TEG has been regenerated, it is then recycled for reuse in the dehydration system. The TEG is recirculated numerous times per hour through the entire dehydration system(absorber tower and regenerators).

In normal use a supply of TEG will run for several months before it gets so laden with impurities that it is no longer efficient to continue use. Many of the contaminants are hazardous materials requiring expensive limitations upon their disposal. This refining unit is preferably mounted on a trailer so that it may be moved to a dehydration system where it is needed to refine or purify the spent TEG and return it to storage for reuse. The TEG can also be used to clean the dehydrator. Those in the art will understand that the dehydrators become loaded with contaminants which are hazardous, which in turn, requires expensive disposal. However, with this process, the TEG can be circulated through the dehydrator system and greatly reduce the volume of material requiring disposal.

For background information relating to glycol dehydration systems for treating natural gas, reference may be had to U.S. Pat. Nos. 5,163,981; 5,116,393; 4,375,977 and 4,661,130.

The problems encountered with TEG dehydrators is that along with water, the TEG starts to pick up small amounts of light liquid hydrocarbons. These hydrocarbons are not as easily removed as the water in the regeneration phase and a certain amount of the hydrocarbons remain with the lean TEG as it circulates back through the absorber column. The hydrocarbons attract other contaminants along with more hydrocarbons that are found in the gas stream and the TEG becomes further diluted with pollutants. As the TEG becomes more saturated, contaminants and hydrocarbons are increasingly more difficult to remove in the regeneration process. Some aromatic hydrocarbons are passed along with the water vapor into the atmosphere. These aromatic hydrocarbons are considered pollutants. They include benzene, toluene, ethylene and xylene, commonly known as BTEX. They are environmentally hazardous and considered carcinogens. These and other hydrocarbons that may be generated in the process of dehydrating natural gas are referred to as volatile organic compounds (VOC). The control of BTEX and other VOC emissions from TEG dehydration units is of increasing concern to environmental protection both at the federal and state levels. Air quality regulations in the United States are increasing because of the Clean Air Act Amendments (CAAA) of 1990. Other regulations include the National Emission Standard Hazardous Air Pollutants (NESHAP) program and state regulatory agencies.

Another source of contamination to the TEG system is salts. Carry over of brine solutions from the field can lead to salt contamination in the TEG system. Sodium salts (typically sodium chloride) are a source of problems in the reboiler since sodium chloride is less soluble in hot TEG than in cool TEG. Salts will precipitate from the solution at typical reboiler temperatures of 350 to 400 degrees Fahrenheit at atmospheric pressure. The salt can deposit on the fire tube restricting heat transfer, causing the temperature of the fire tube increase, which will lead to thermal degradation of the TEG. The salt will also increase corrosion of the fire tube. The dissolved salts cannot be removed by mechanical filtration. When the salt content reaches 1% the TEG is spent and should be reclaimed or replaced.

After a period of time, the TEG becomes severely contaminated and loses its effectiveness as a desiccant and is considered "spent". TEG at 94% concentration in solution becomes increasingly ineffective as a desiccant. The presence of contaminants may result in fouled equipment, foaming, poor dehydration and the potential of increased release of pollutants into the atmosphere. The options for spent TEG are to dispose of it and replace it with new TEG. The spent TEG may also be sent to a reclaimer for recovery. (Both of which are not very economic and will require the dehydration system to be shutdown.) During these down times operators currently choose to clean the dehydration system at considerable costs, which produces large amounts of hazardous waste to be disposed of. This also increases the chance of spilling the hazardous waste onto the ground causing more problems.

SUMMARY OF THE INVENTION:
(1) Progressive Contribution to the Art

According to this invention, the glycols may be cleaned and recycled by vacuum distillation. The glycols have an evaporation temperature at atmospheric pressure higher than the temperature at which they degenerate. It is necessary to evaporate them at a temperature below the point that they degenerate. The evaporation temperature is elevated as high as possible but still must be below the degeneration point. The absolute pressure is reduced on the evaporating liquids on a economy basis. The absolute pressure is reduced as low as possible for rapid evaporation and temperatures no higher than necessary. However, to obtain extremely low absolute pressures is difficult and expensive. Therefore the pressure used for evaporation is one that is a balance between these considerations.

An improved process of refining TEG is provided in which the unit is a mobile self contained unit that will purify the spent TEG by substantially reducing the amount of entrained solids and hydrocarbons. The refining unit can also be used to clean contacting towers, heat exchangers, pumps, still column, reboiler and surge tanks of TEG dehydrators. This will provide a 97% volume reduction in hazardous wastes compared to conventional methods of cleaning dehydrators. The unit accomplishes this with vacuum distillation incorporating a closed system. The refining unit utilizes the TEG located at the site along with a chemical degreaser that aids in the removal of coke and sludge buildups. All contaminants and foulants that are removed from the contacting tower of the dehydration system are removed by the refining unit. The unit eliminates the risk of hazardous waste spills that commonly occur with conventional cleaning methods of dehydration systems. All wastes that occur during cleaning and refining are gathered in the refining unit. These wastes can be collected very easily to be disposed of properly. The refining unit will provide efficient cleaning of dehydration equipment, reduce hazardous waste volume, convert hazardous waste into a useful product, reduce the emission of dangerous VOC's and BTEX all without shutting in gas sales. The refining unit is able to accomplish this since it is a closed system. The unit can utilize dehydrated gas or LPG at the site for fuel gas for the burner, power medium used in the operation of valves, shutdowns and fluid transfer.

The refining unit is kind to the environment by utilizing spent solution in a cleaning process, returning a spent solution to its usable form, recycling spent solution which eliminates the need to produce more solution, eliminating the emission of hazardous VOC's and BTEX during refining, reducing the emission of VOC's and BTEX in TEG dehydration units, reducing hazardous waste that can be created during a cleaning operation, eliminating the risk of soil contamination due to hazardous spills, simplifies the collection of hazardous waste at the site and accomplishing all of the aforementioned while the dehydration system continues gas sales.

This invention also is used to recycle glycols used as anti-freeze. It is more economical to gather the used anti-freeze and transport it to a stationary recycling plant.

This invention reduces if not completely prevents the release of BTEX gases into the atmosphere. This invention reduces by 97% the amount of hazardous waste from the polluted glycol. It eliminates the added industrial hazard of the conventional cleaning of the polluted gas plant equipment. The normal cleaning of the equipment greatly increases the volume of the hazardous waste; making up to five times as much hazardous waste as originally present because of the volume of the polluted cleaning fluid. The immediate vicinity is protected by the use of a completely closed system.

This process has the following unique features and advantages:

(1) To purify the TEG with the unit requires only one cycle.
(2) Self containment of the TEG refining process, hydrocarbon adsorption process and dehydration system cleaning process, thus the equipment of the refining unit may be mobile.
(3) Process that reduces a contaminated waste product to the lowest possible volume for disposal while purifying TEG and cleaning dehydration systems.
(4) Recycles contaminated TEG instead of the disposing of contaminated TEG and replacing with new TEG at approximately 50% of the replacement costs.
(5) Reduces disposal of hazardous waste by over 95%.
(6) Allows user to produce natural gas uninterrupted while purifying TEG in the refining unit.
(7) Allows user to produce natural gas uninterrupted while cleaning the dehydration system.
(8) Reduces waste disposal generated while cleaning dehydration system from 100% to 1% by volume.
(9) Does not emit hazardous VOC's and BTEX.
(10) Provides the process in closed system eliminating the risk of hazardous waste spills.
(11) Helps reduce hazardous air emissions from dehydrator units.
(12) Improves gas/glycol contacting resulting in better water removal.
(13) Eliminates foaming stopping uncontrolled glycol losses.
(14) Reduces the risk of salt contamination in the dehydration system which can cause hot spots on the fire tube, thermal degradation of the TEG and increase corrosion in the dehydrator system.

(2) Objects of this Invention

An object of this invention is to recycle glycols for reuse.

Another object of this invention is to recycle glycol from a natural gas dehydration plant and simultaneously clean the equipment of the natural gas plant to both rejuvenate the glycol and to concentrate and remove the hazardous waste from the natural gas plant.

A further object of this invention is to recycle glycols used as anti-freeze.

Further objects are to achieve the above with devices that are sturdy, compact, durable, lightweight, mobile, simple, safe, efficient, versatile, ecologically compatible, energy conserving, and reliable, yet inexpensive and easy to manufacture, install, operate, and maintain.

Further objects are to achieve the above with a method that is rapid, versatile, ecologically compatible, energy conserving, efficient, and inexpensive, and does not require highly skilled people to install, operate, and maintain.

The specific nature of the invention, as well as other objects, uses, and advantages thereof, will clearly appear from the following description and from the accompanying drawings, the different views of which are not necessarily scale drawings.

CATALOGUE OF ELEMENTS:
As an aid to correlating the terms of the claims to the exemplary drawing(s), the following catalog of elements and steps is provided:

| | |
|---|---|
| 9 | source of contaminated glycol |
| 10 | conduit |
| 11 | check valve |
| 12 | inlet control valve |
| 13 | surge tank |
| 14 | valve |
| 15 | gate valve |
| 16 | line |
| 17 | heating coil |
| 18 | pump valve |
| 19 | vacuum reboiler or evaporator |
| 20 | burner |
| 22 | pre-condense air cooler |
| 25 | wye-strainer |
| 27 | vacuum pump |
| 28 | wye strainer |
| 29 | air cooler |
| 31 | seal oil tank |
| 33 | transfer pump |
| 35 | particle filter |
| 36 | carbon filter |
| 37 | outlet line |
| 38 | bypass line |
| 39 | temperature switch |
| 40 | burner supply valve |
| 41 | pilot regulator |
| 42 | pilot line |
| 43 | burner supply line |
| 44 | float switch |
| 45 | pump float switch |
| 46 | two-way valve |
| 47 | pressure regulator |
| 48 | inlet line |
| 49 | temperature switch |
| 50 | seal oil cooler |
| 51 | regulator |
| 52 | vapor chamber |
| 53 | gas accumulator |
| 54 | chemical injection tank |
| 55 | ball valve |
| 60 | trailer |
| 62 | base structure |
| 64 | wheels |
| 66 | trailer hitch |
| solid line = glycol | |
| irregular dash lines = cleaning agent | |
| dashed lines = natural gas | |

DESCRIPTION OF THE PREFERRED EMBODIMENTS(S)

When used with a natural gas dehydration plant this invention is designed to remove impurities from TEG.

Figure 1:
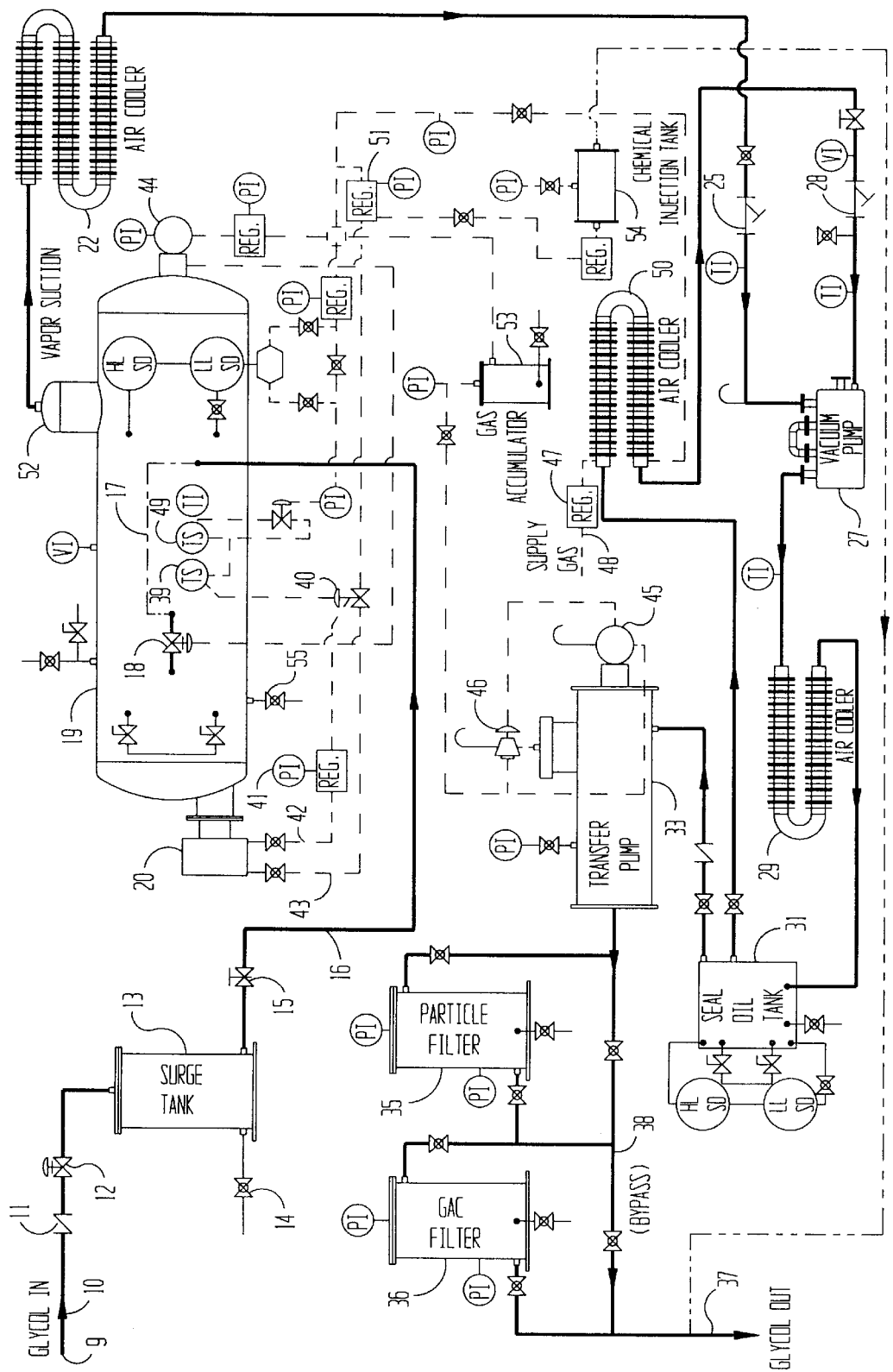
FIG. 1 is a flow schematic diagram of the glycol refining process in which the present invention is embodied.

Referring to FIG. 1 there is shown a schematic flow sheet showing the equipment for the glycol refining process embodying the present invention. The processing of the contaminated glycol can be conducted on a batch or semi batch process. Spent TEG is brought into the system by vacuum and/or gravity. The natural gas dehydration plant is a source 9 of contaminated TEG for the refining equipment. The spent glycol enters the system in a conduit 10 that then passes through a check valve 11. The spent glycol then flows through the inlet control valve 12 and into the surge tank 13. The inlet control valve 12 is controlled by high and low level shutdowns located in vacuum reboiler or evaporator 19 and seal oil tank 31. When a low or high level shutdown occurs the inlet control valve 12 is shut and a temperature switch 49 cuts off the fuel supply to burner 20.

After the spent TEG is received in the surge tank 13 it then passes through a gate valve 15 into line 16. The spent TEG then passes through a heating coil 17 located inside the vacuum reboiler 19. The spent TEG then flows through dump valve 18, where the level inside the vacuum reboiler 19 is controlled by a float switch 44. When the float switch indicates that additional spent TEG is required in the vacuum reboiler 19 the dump valve 18 opens. The dump valve 18 remains open until the float switch 44 is tripped and the dump valve 18 is closed.

Supply gas is used to operate pressure regulator valves, and "pump" TEG from transfer pump 33 (as described later) as well as to fire the burner 20 and "pump" cleaning chemical from chemical injection tank 54 to the dehydration system. The source of the supply gas may be methane from the dehydration plant or from bottled liquid petroleum gas (LPG) such as propane.

The supply gas enters the system through inlet line 48 where the supply pressure is set by regulator 47. The supply gas is then passed through seal oil cooler 50 which aids in vaporizing the LPG if used.

Fuel to the burner 20 is supplied by regulator 51 where the fuel passes through burner supply valve 40 to burner supply line 43. The temperature in the evaporator vacuum reboiler 19 is maintained at about 400 degrees Fahrenheit. This is accomplished by the reboiler temperature switch 39. The pilot gas for the burner 20 is supplied through a regulator 41 to pilot line 42.

A burner with a flame tube submerged in the spent glycol is used to heat the vacuum reboiler. The boiler is sufficiently sized to provide adequate retention time to allow the suspended solids to settle out by gravity acting as a settling basin. The small amount of sludge that will be produced in the bottom of the vacuum reboiler must be removed and disposed of as hazardous waste.

The spent TEG is flashed as it is heated at 400 degrees Fahrenheit within the vacuum evaporator or reboiler 19 while being subjected to a vacuum of 20–22 inches of mercury or an absolute pressure of about 9 inches Hg. The vapors that are produced are removed through vapor chamber 52 of the vacuum reboiler 19. The vapors then pass through pre-condense air cooler 22. The vapors are cooled within the air cooler 22 to a temperature so that about 30% of the vapors are condensed before they enter vacuum pump 27. The vacuum pump 27 provides the desired vacuum. A manually controlled throttle valve on the pump allows the operator to adjust the vacuum. The vacuum may vary over a range of +/−7 inches of mercury. A Wye (or Y)-strainer 25 is located before the vacuum pump 27 to remove any scale that may remain in the condensed TEG.

The partially condensed vapors from the vacuum pump are then passed through another air cooler 29 where the vapors are completely condensed and then stored in the seal oil tank 31. A small amount of the condensed TEG will be used as seal oil for the vacuum pump 27. The seal oil is pulled by vacuum to the vacuum pump 27 from the seal oil tank 31, through the air cooler 50. The cooling of the seal oil is further enhanced by passing the supply gas through the air cooler 50. The seal oil is then passed through a Y-strainer 28 to the vacuum pump 27. The seal oil is used to seal the ends of the vanes against the housing on the turbine type vacuum pump 27.

Liquid TEG from the seal oil tank 31 flows by gravity to the transfer pump 33. As TEG accumulates in the transfer pump 33, a float switch 45 located inside the transfer pump 33 will actuate the two-way valve 46. This will pressurize the transfer pump 33 and disperse any fluid contained. As the transfer pump 33 begins to empty it will trip the float switch 45 again actuating the two-way valve 46 and venting the transfer pump 33 to atmosphere. The transfer pump 33 will again allow TEG to accumulate until the float switch 45 is tripped again. Supply gas used in powering the transfer pump 33 is stored in a gas accumulator 53. The transfer pump 33 forces the TEG through particle filter 35, granular activated carbon filter 36, and outlet line 37 to a clean TEG storage tank.(Not Shown)

The solution then passes through a granular activated carbon filter that will remove any BTEX, VOC's, hydrocarbons, surfactants, well treating chemicals, compressor lubricants and TEG degradation products. The adsorption process is more effective after the vacuum dehydration and recondensing of the solution. The vacuum process allows the unit to conduct a reversible adsorption process on the TEG by adsorbing the dissolved hydrocarbons.

The particle filter 35 is used to remove any entrained solids or scale. The granular activated carbon filter 36 is used to remove any hydrocarbons. This is the final step in the refining process and the finished product may be returned to the dehydrating system via the clean TEG storage tank.

When it is necessary for the dehydrating system to be cleaned the purified TEG may be used. The condition of the dehydration system equipment may be determined by visual and laboratory inspection of incoming glycol sampled at valve 14. A chemical injection tank 54 is provided on the refining unit to assist in the cleaning process. The chemical injection tank 54 is pressurized using the supply gas. The TEG and cleaning chemical is circulated through the dehydrating unit continuously until the dehydrating unit is cleaned. The TEG and cleaner will remove sludge and coke build up in the dehydration system. The TEG that is circulated will become contaminated and will be returned to the TEG refining unit. The cleaning process will be done continuously until both the TEG and dehydrating system are clean. All wastes that are developed during cleaning are contained in the closed system so that they may be disposed of properly without the risk of spillage. A chemical injection tank is provided on the refining unit to enhance the cleaning process. The chemicals used in the refining unit are a degreaser and sometimes a water based cleaner. The cleaner is non-acidic and non-alkaline and is classified as a noncorrosive. The cleaner is only slightly toxic to daphnia magna (water flea) and bacterial populations at concentrations well above those expected to be encountered. The degreaser is only moderately toxic to daphnia magna and fathead minnows and it is relatively noninhibitory to bacterial populations. Both the cleaner and degreaser biodegrade rapidly. The degreaser contains no volatile organic solvents, halogenated solvents, inorganic phosphates or other alkalinity builders. The cleaner, if necessary, removes all mineral scales, rust and other forms of corrosion. The degreaser removes all hydrocarbon based foulants. When the hydrocarbon based foulants are removed, usually the other contaminates are removed by clean glycol. Solution strengths range from 5 to 25 volume percent depending upon the scale and foulants to be removed from the dehydration system. The solution depletion is measured by the pH and if the solution drawn at valve 14 remains at a constant value at or below 8 for an extended period the dehydration system is probably clean. The operator cleans the unit on this basis and visual examination and runs the cleaning cycle until the pH of the solution remains steady at 8. The TEG can be refined as mentioned above after the cleaning process is done free of all contaminants and returned to the clean holding tank where it is ready for reuse in the TEG dehydration system. Both the refining and cleaning process can be done while the dehydration system remains in operation without shutting in gas sales. The TEG can then be passed through the granular activated carbon 36 to remove any hydrocarbons and then be placed in a clean storage tank.

The preferred cleaning agent if used is NORKOOL Industrial Heat Transfer System Cleaner, N801, NORKOOL degreaser DG/E803 is the preferred degreaser. Both products of Union Carbide Corporation, Danbury, Conn. and are available from the Houston, Tex. location of the Union Carbide Corporation. Both these products meet the requirement that they are non-acidic and non-alkaline and also classified as noncorrosive and are referred to as cleaning agents.

In the operation, a standard chemical injection system is used which permits a regulated flow of the additive to a measured amount of glycol. Such units are well known and commonly available on the market. In this use, the cleaning agents will be used anywhere from 5% of the volume of glycol to as much as 25% of the volume of glycol. Stated otherwise this is a ratio of one part of cleaning agent to 20 parts of glycol to as much as one part of cleaning agent to 4 parts of glycol.

Normally the degreaser would initially be used at about 10% (one part cleaning agent to ten parts glycol). With this use the glycol would continually be sampled as it entered the recycling unit, at valve 14. If the glycol at this point had a pH of 8, the treatment would be continued and if no particular progress was noted, the amount of cleaning agent per glycol could be increased till favorable results were observed. At the point when the pH of the entering glycol is below 8 and is clear and not changing, it will be considered that the unit has been cleaned.

Both the cleaner N801 and the degreaser E803 are considered to be cleaning agents as the term is used in this application. The need for the degreaser will also be apparent if the glycol shows a above normal amount of hydrocarbons at the valve 14. Again in the use of the degreaser, it may be used in any ratio, from 5% of the volume of glycol to as much as 25% of the volume of glycol.

Caution must be used in using an excessive amount of cleaning agent in as much a excessive release of the contaminants on the equipment of the dehydrator will cause operating problems with the natural gas dehydrating process.

Hazardous materials will collect in the bottom of the vacuum reboiler 19 and will be removed through a ball valve 55. The hazardous sludge will be removed by first heating the reboiler 19 to about 400 degrees Fahrenheit at atmospheric pressure or higher. This will liquefy the sludge and force it out. The small amount of hazardous sludge will be collected and disposed of as hazardous material. Wye strainers 25 & 28 will also require periodic cleaning and this very small amount of waste should also be disposed of as hazardous material.

The filter elements used in this invention will need to be replaced regularly to maintain solution quality. The granular activated carbon 36 and particle filter 35 will constitute a solid waste requiring proper disposal.

Figure 2:
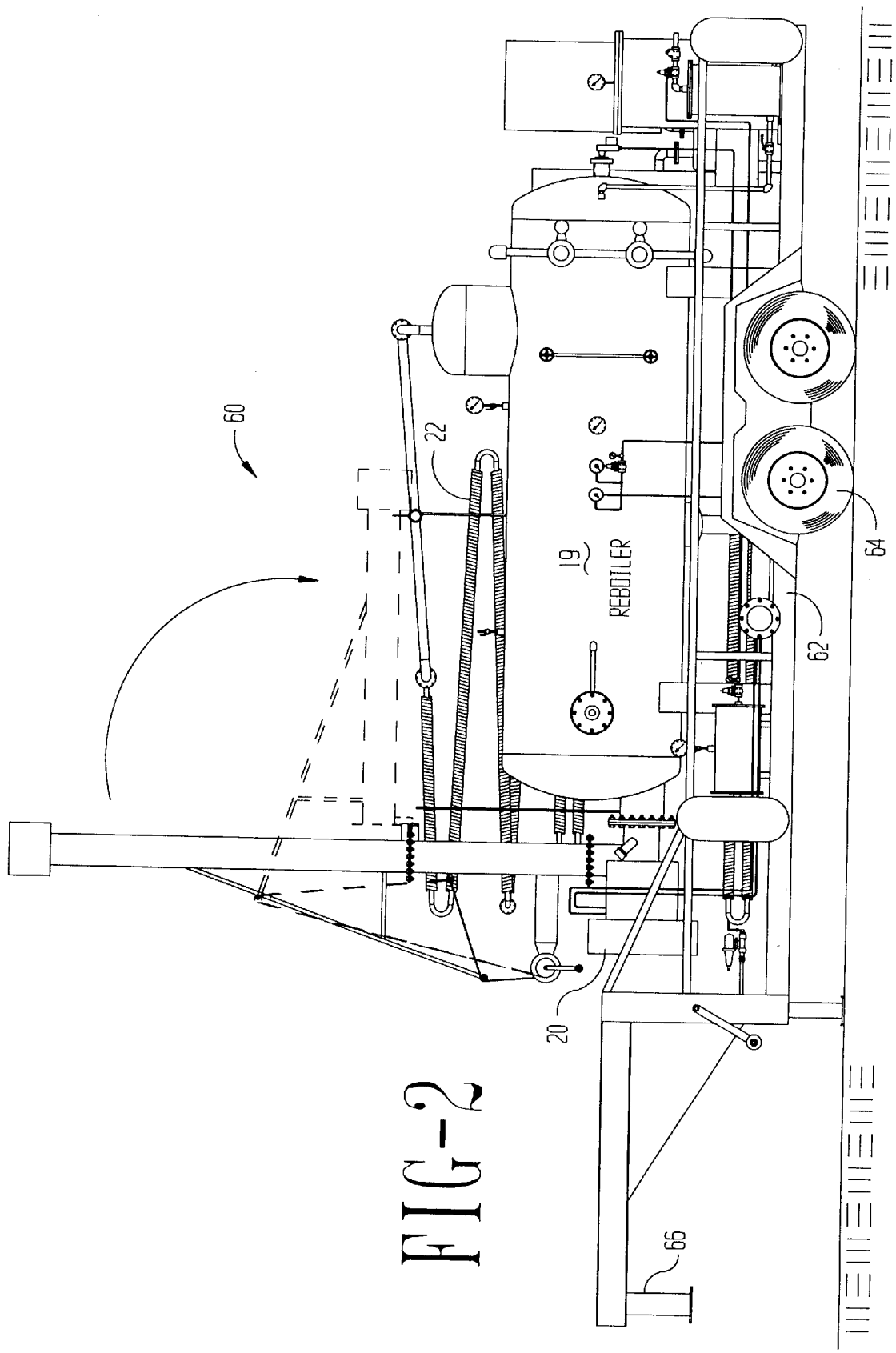
FIG. 2 is a schematic of the trailer.

Vacuum is supplied by means of an electric motor driven pump 27. This is the preferred arrangement when electrical energy is conveniently and economically available. In some locations where it is necessary to dehydrate natural gas, electrical energy is not available or, at least, is not available on economic terms. In this case a gas or gasoline driven vacuum pump 27 may be used. An electric generator that is driven by a natural gas engine may be used to provide electric power in remote locations As set out above that the rejuvenation of the glycol in a natural gas dehydration plant maybe only required about once a year and also may take no more than three or four days to rejuvenate the glycol. Therefore it is desirable to have the equipment mobile so that it can be moved from one natural gas dehydration plant to another. To accomplish this all of the references made to FIG. 2. There may be seen that all the equipment necessary to accomplish the dehydration, although not necessarily shown in FIG. 2, may be mounted upon a trailer 60. The trailer will have a base structure or bed 62 upon which all of the equipment is mounted. The trailer will have wheel 64 and a trailer hitch 66 so that it can be moved from one unit to another. When it is moved to a unit, the conduit 10 will be connected to the gas plant and the gas plant will serve as a source 9 of contaminated glycol for the refining equipment mounted upon the base structure of the trailer. Also, the conduit 37 from the carbon filter 36 will be connected to the dehydration plant.

Although it is preferred that the equipment be mounted upon a trailer, those skilled in the art will understand that it could be also other types of mobile structures, for example, a skid loaded upon a flatbed tractor trailer to be moved from one location to another. Also other mobile structures might be used.

Also as stated above the unit is also useful in refining ethylene glycol and diethylene glycol which are used as anti-freezes. In such an instance, it is more economical to bring the spent or contaminated glycol to the refining unit. In this event, the refining unit might well be the equipment mounted upon a mobile structure which is located at some convenient location. If the anti-freeze to be refined is ethylene glycol it will be understood that the evaporator temperature can be about 240° F. at which point the ethylene glycol will evaporate rapidly at nine inches of Hg. absolute pressure. This adjustment of the temperature of the evaporator can readily be made by the controls which would normally control its temperature at about 400°. Likewise if the anti-freeze glycol the temperature of the evaporator would be about 255° F.

Also since the equipment is in place, it can be operated at a pressure of nine inches of Hg. absolute. As set out above that the amount of vacuum which is pulled upon the evaporator is balance between the difficulty of obtaining high vacuums and the convenience of operating the equipment at large volume and the constraints that the temperature of the evaporator is limited by the degradation point of the glycol being refined. In this regard it is noted that there is about a +/−7 p.s.i. variance so that the vacuum that the evaporator operates at for any of the glycols might vary from as low as 2 inches of Hg. absolute to as much as 16 inches Hg. absolute.

The embodiment shown and described above is only exemplary. I do not claim to have invented all the parts, elements or steps described. Various modifications can be made in the construction, material, arrangement, and operation, and still be within the scope of my invention.

While the invention has been described in relation to certain preferred embodiments, it is apparent to those skilled in the art that changes may be made to the arrangement of the components and it is susceptible to additional embodiments without departing from the basic principles of the invention.

The restrictive description and drawings of the specific examples above do not point out what an infringement of this patent would be, but are to enable one skilled in the art to make and use the invention. The limits of the invention and the bounds of the patent protection are measured by and defined in the following claims.

I claim as my invention:

1. A process for the refining of hazardously contaminated Triethylene glycol (TEG) comprising:
    a) continuously supplying a contaminated TEG from a natural gas dehydration plant equipment to a vacuum reboiler;
    b) heating said contaminated TEG to a temperature of approximately 400 degrees Fahrenheit in the vacuum reboiler; while
    c) subjecting said contaminated TEG in the reboiler to a vacuum of 20 to 22 inches of mercury; thus
    d) causing flash vaporization of said contaminated TEG in the vacuum reboiler thereby creating separated contaminants and a vaporized TEG; then
    e) withdrawing said vaporized TEG from said vacuum reboiler; then
    f) passing said vaporized TEG through an air cooler and partially condensing the TEG; then
    g) pumping said partially condensed TEG through a vacuum pump, then through a second air cooler, thus fully condensing the TEG; then
    h) storing the fully condensed TEG in a tank; then
    i) moving the TEG to a transfer pump; then
    j) moving said TEG from said transfer pump to a particle filter; then
    k) passing said TEG from said particle filter to a granular activated carbon filter thus forming refined TEG;
    l) continuously circulating the refined TEG to the natural gas dehydration plant equipment while the dehydration plant equipment is in operation; and
    m) removing separated contaminants from a bottom of the vacuum reboiler.

2. A process in accordance with claim 1, further comprising:
    n) mounting equipment performing the above process upon a trailer and moving the trailer from one natural gas dehydration plant to another natural gas dehydration plant.

3. A process in accordance with claim 1 wherein said refined TEG can be used in cleaning dehydration equipment while reducing contaminated waste product 97% by volume for disposal.

4. A process in accordance with claim 1, wherein said contaminated TEG is refined to 99.7% concentration solution in one cycle.

5. A process in accordance with claim 1, wherein said refined TEG is formed from contaminated TEG at approximately 50% of a replacement cost.

6. A process in accordance with claim 1, wherein more than 99% of the contaminants are separated from the TEG in the flash vaporization of step d).

* * * * *